US009132042B2

(12) United States Patent
Nakakado

(10) Patent No.: US 9,132,042 B2
(45) Date of Patent: Sep. 15, 2015

(54) DEVICE FOR MANUFACTURING ABSORBENT ARTICLE

(71) Applicant: Masaki Nakakado, Osaka (JP)

(72) Inventor: Masaki Nakakado, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 14/407,619

(22) PCT Filed: Jun. 13, 2013

(86) PCT No.: PCT/JP2013/066325
§ 371 (c)(1),
(2) Date: Dec. 12, 2014

(87) PCT Pub. No.: WO2014/010365
PCT Pub. Date: Jan. 16, 2014

(65) Prior Publication Data
US 2015/0144270 A1    May 28, 2015

(30) Foreign Application Priority Data

Jul. 13, 2012    (JP) ................. 2012-157093

(51) Int. Cl.
*B32B 37/00*    (2006.01)
*A61F 13/15*    (2006.01)
(Continued)

(52) U.S. Cl.
CPC ........... *A61F 13/15634* (2013.01); *A61F 13/15* (2013.01); *A61F 13/15658* (2013.01); *A61F 13/15699* (2013.01); *A61F 13/49* (2013.01); *A61F 13/53* (2013.01); *A61F 13/5323* (2013.01); *B29C 65/08* (2013.01); *B29C 65/086* (2013.01); *B29C 65/087* (2013.01);

(Continued)

(58) Field of Classification Search
CPC ................ A61F 13/5323; A61F 13/49; A61F 13/15699; A61F 13/15658; B29C 65/086; B29C 65/087; B29C 65/7847; B29C 66/21; B29C 66/232; B29C 66/433; B29C 66/81433; B29C 65/08
USPC .................................. 156/73.1, 580.1, 580.2
See application file for complete search history.

(56) References Cited

U.S. PATENT DOCUMENTS 4,109,353 A *   8/1978   Mitchell et al. ................. 28/104
6,165,298 A *  12/2000   Samida et al. ............... 156/73.1
(Continued)

FOREIGN PATENT DOCUMENTS

JP    2007-130818 A    5/2007
JP    2008-507384 W    3/2008
(Continued)

OTHER PUBLICATIONS

International Search report for corresponding International Application No. PCT/JP2013/066325 mailed Sep. 3, 2013.

*Primary Examiner* — James Sells
(74) *Attorney, Agent, or Firm* — Renner, Otto, Boisselle & Sklar, LLP

(57) ABSTRACT

A device including: a plurality of protruding portions of an anvil roll; an ultrasonically vibrating horn; a suction hole for drawing granular particles together with non-woven fabric sheets so as to carry the non-woven fabric sheets and to prevent the granular particles from being placed on the non-woven fabric sheets over the protruding portions; and a ridge extending along an outer circumference of the suction hole with a protruding height lower than a protruding height of the protruding portions.

7 Claims, 9 Drawing Sheets

(51) Int. Cl.
   *A61F 13/532* (2006.01)
   *B29C 65/08* (2006.01)
   *B29C 65/78* (2006.01)
   *B29C 65/00* (2006.01)
   *A61F 13/49* (2006.01)
   *A61F 13/53* (2006.01)
   *B29L 31/48* (2006.01)

(52) U.S. Cl.
   CPC ......... *B29C65/7847* (2013.01); *B29C 66/1122* (2013.01); *B29C 66/21* (2013.01); *B29C 66/232* (2013.01); *B29C 66/433* (2013.01); *B29C 66/7294* (2013.01); *B29C 66/7373* (2013.01); *B29C 66/81433* (2013.01); *B29C 66/83511* (2013.01); *A61F 2013/53051* (2013.01); *A61F 2013/530554* (2013.01); *B29C 66/73921* (2013.01); *B29C 66/83433* (2013.01); *B29L 2031/4878* (2013.01)

(56) References Cited

U.S. PATENT DOCUMENTS

| 7,204,899 B2 * | 4/2007 | Van Eperen ................. 156/73.3 |
| 2006/0021695 A1 | 2/2006 | Blessing et al. |
| 2012/0226253 A1 | 9/2012 | Urushihara |
| 2013/0025795 A1 | 1/2013 | Ukegawa et al. |
| 2013/0284361 A1 | 10/2013 | Tsujimoto et al. |
| 2013/0284362 A1 | 10/2013 | Tsujimoto et al. |
| 2014/0124143 A1 | 5/2014 | Maruhata |

FOREIGN PATENT DOCUMENTS

| JP | 2011-136077 A | 7/2011 |
| JP | 2013-017565 A | 1/2013 |
| WO | WO 2011-105509 A1 | 9/2011 |
| WO | WO 2012/108330 A1 | 8/2012 |
| WO | WO 2012/108331 A1 | 8/2012 |
| WO | WO 2014/007043 A1 | 1/2014 |

* cited by examiner

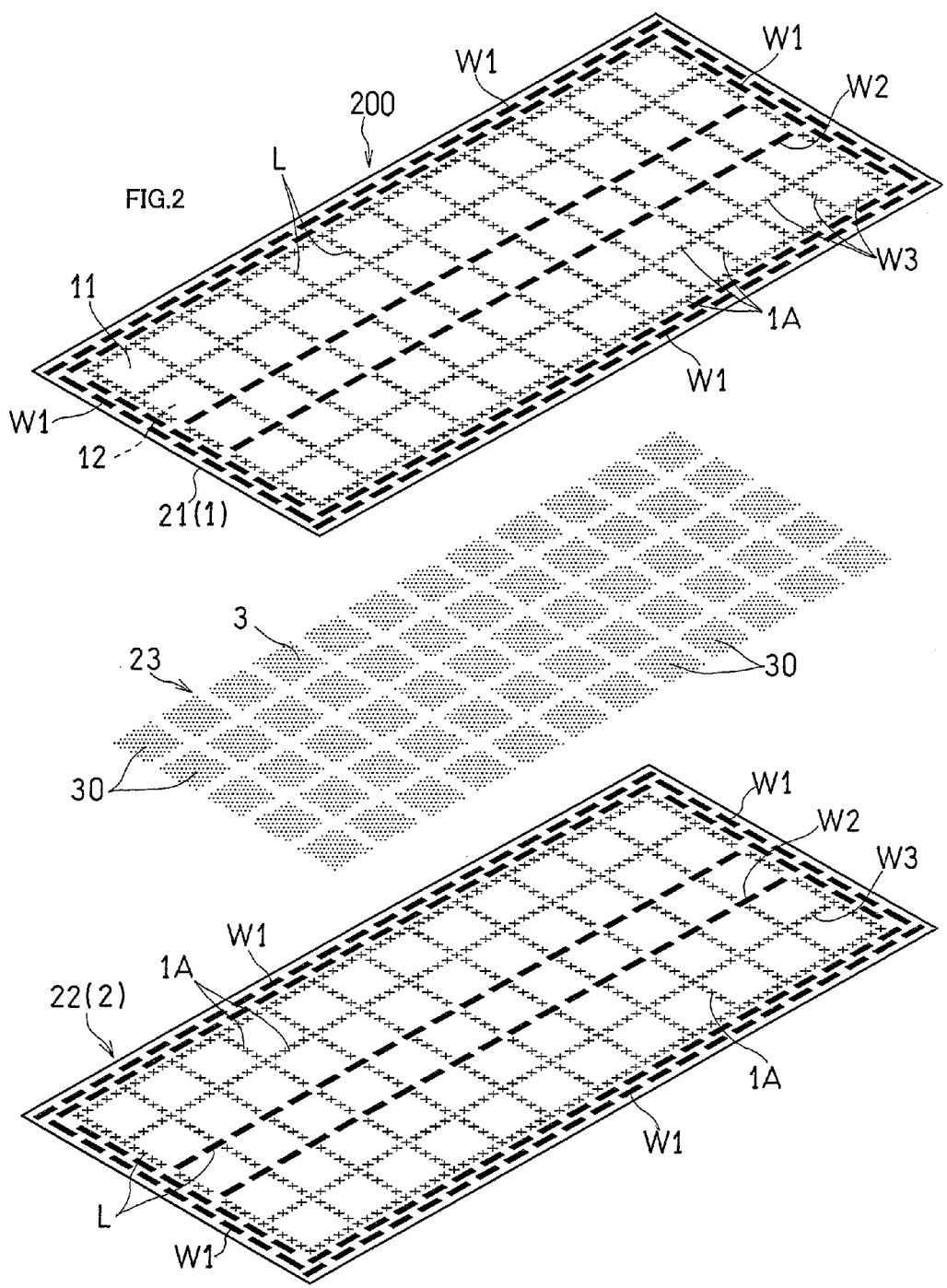

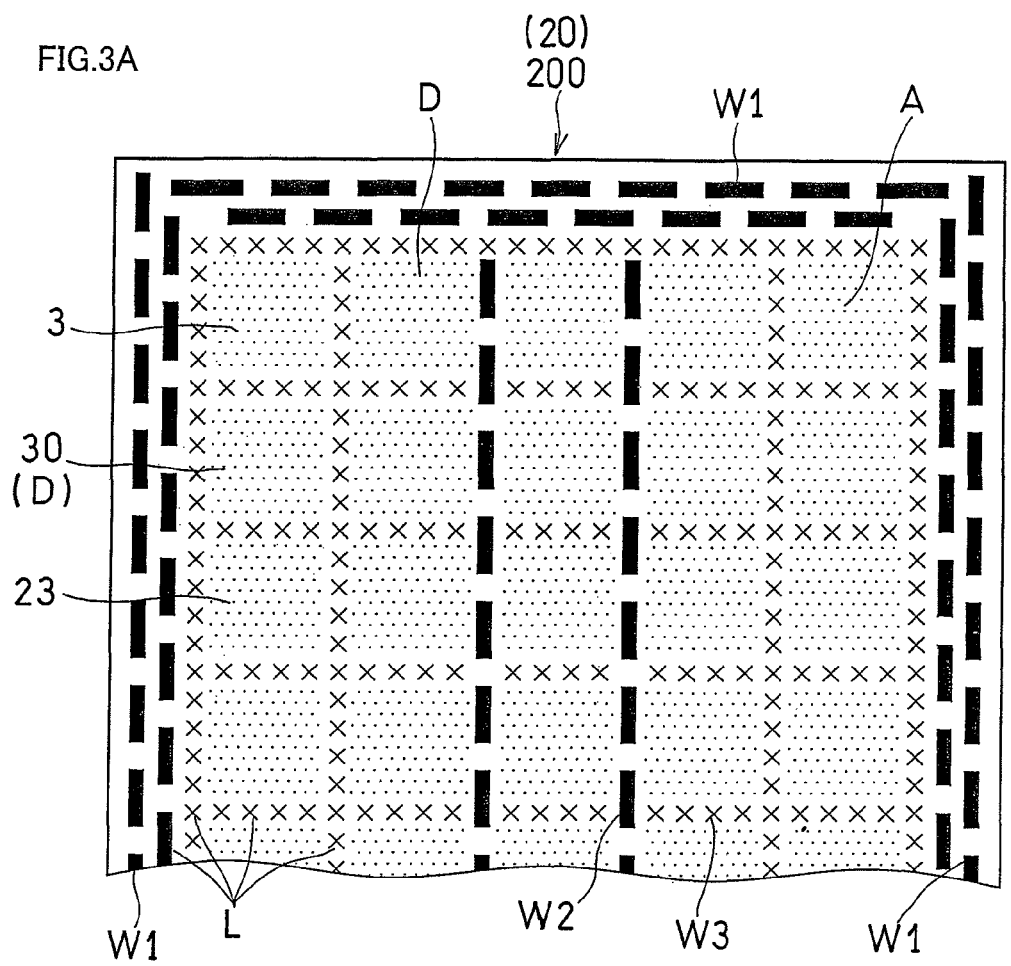
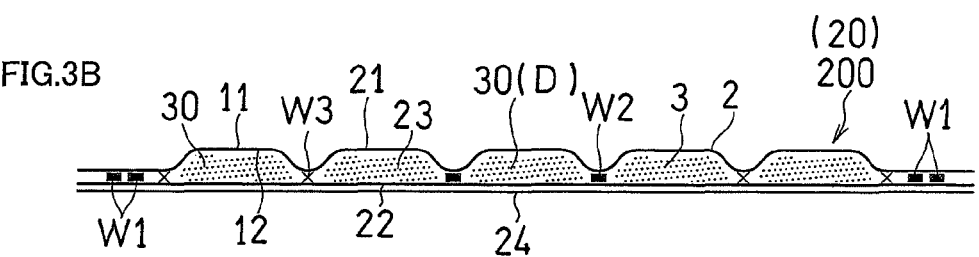
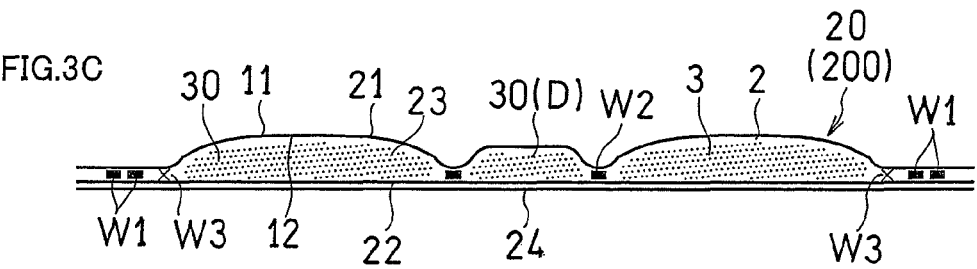

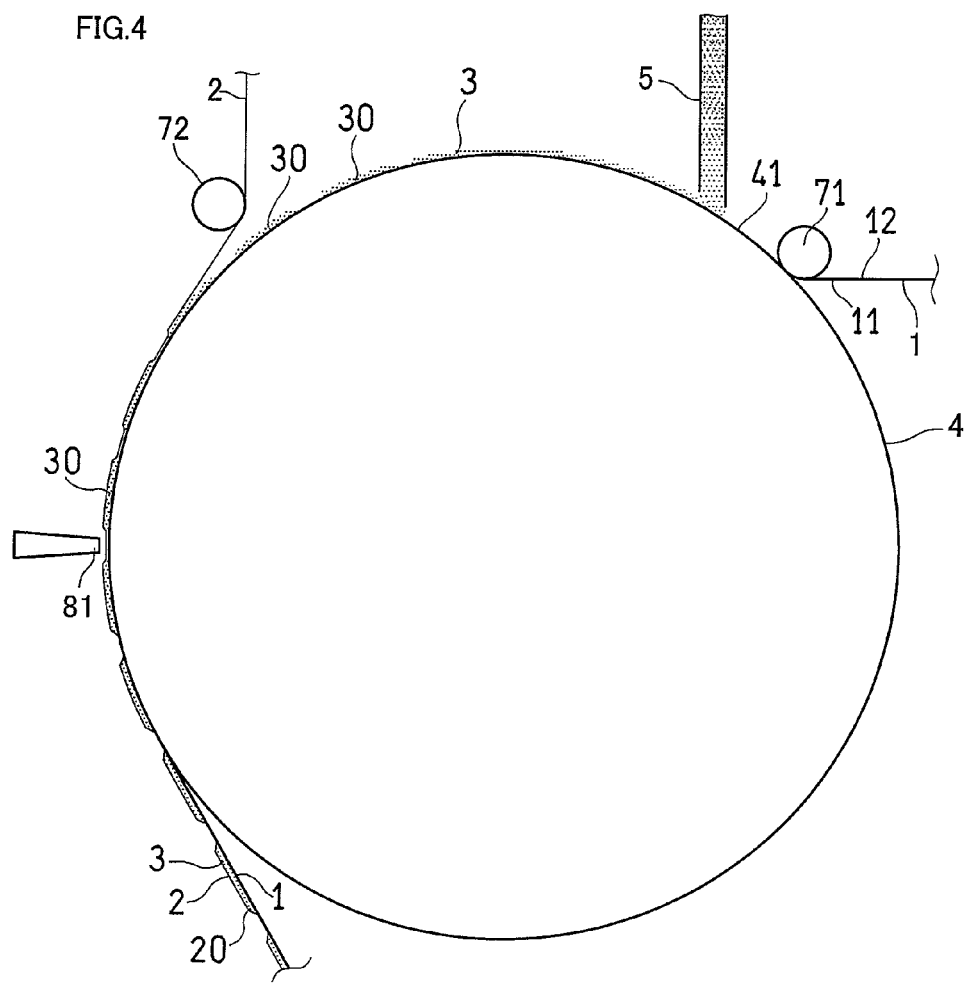

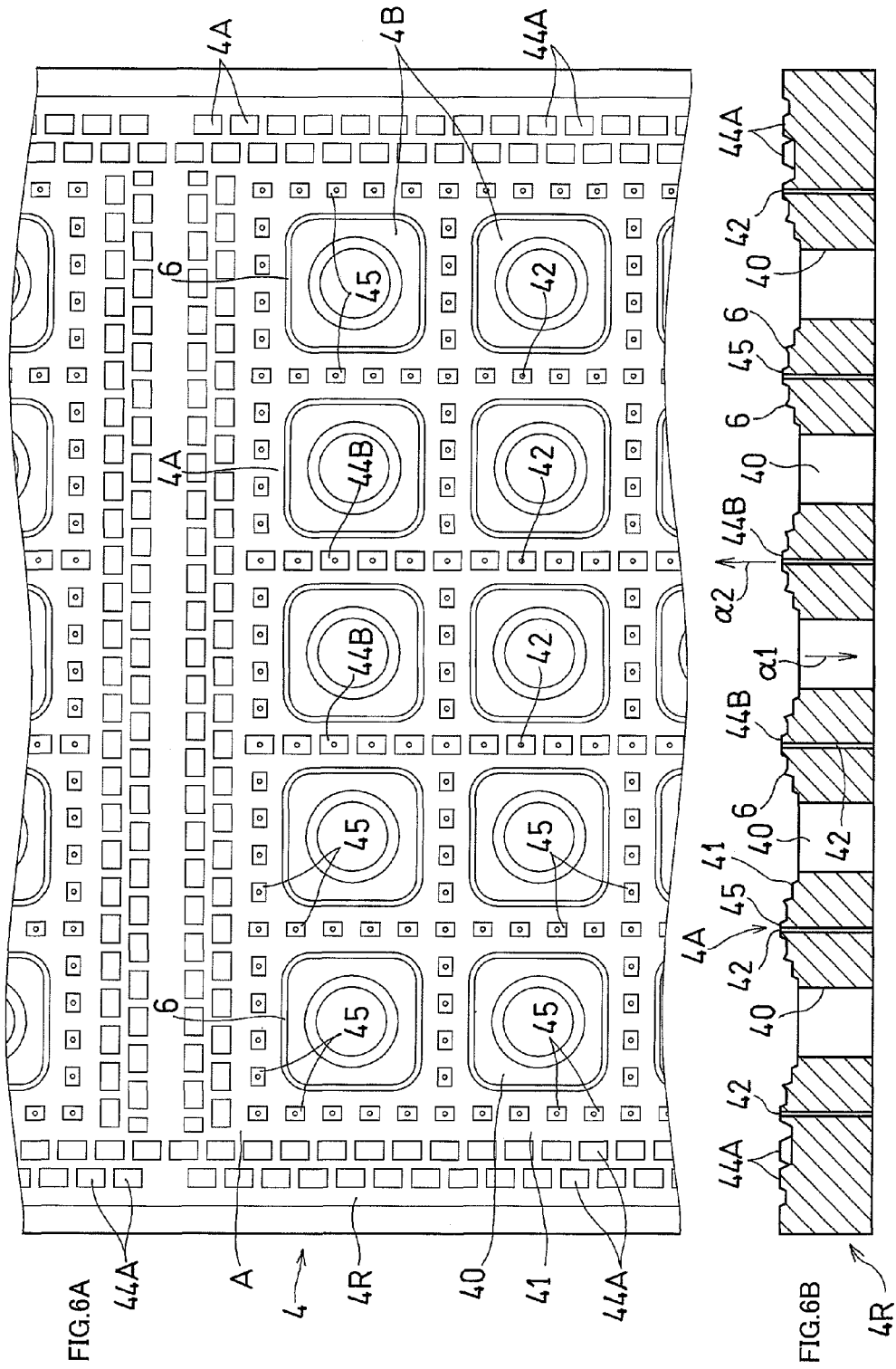

DEVICE FOR MANUFACTURING ABSORBENT ARTICLE

TECHNICAL FIELD

The present invention relates to a device for manufacturing an absorbent article having a large number of granular particles (hereinafter referred to simply as "granular particles") capable of absorbing a body fluid.

BACKGROUND ART

In recent years, a method for manufacturing an absorbent article has been proposed in the art (the first patent document), in which the granular particles of a superabsorbent resin are placed by suction in a predetermined pattern on a base sheet, so that the granular particles are sandwiched between the base sheet and another base sheet, and the base sheets are ultrasonically bonded together at positions where the granular particles are absent.

As the base sheets are ultrasonically bonded together, there is no need to use an adhesive.

CITATION LIST

Patent Literature

[First Patent Document] JP2008-507384 W

SUMMARY OF INVENTION

With ultrasonic bonding, however, if granular particles get caught between a protruding portion of an anvil and a horn in the bonding process, a bonding failure occurs, thereby failing to obtain an intended bonded state or bonding strength. Moreover, in such a case, there may be an adverse influence on assemblies such as the horn or the anvil.

It is therefore an object of the present invention to provide a device for manufacturing an absorbent article, capable of preventing granular particles from getting caught between a protruding portion of an anvil and a horn, thereby making it likely that an intended bonded state or bonding strength will be obtained.

The present invention is directed to a device for manufacturing an absorbent article having a plurality of granular particles capable of absorbing a body fluid between two liquid-permeable non-woven fabric sheets facing each other, the manufacturing device including:

an anvil roll for carrying the two non-woven fabric sheets while the two non-woven fabric sheets are laid on each other;

a plurality of protruding portions formed on the anvil roll so as to protrude outward in a radial direction of the anvil roll; and a horn for ultrasonically vibrating so that the two non-woven fabric sheets are bonded together between the horn and the plurality of protruding portions, thereby forming bonded portions, wherein the anvil roll defines:

at least one suction hole for drawing a first air, through the non-woven fabric sheets, together with the granular particles and the non-woven fabric sheets, so as to carry the non-woven fabric sheets and to prevent the granular particles from being placed on the non-woven fabric sheets over the protruding portions; and a ridge provided between the plurality of protruding portions and the suction hole, the ridge protruding outward in the radial direction of the anvil roll with a protruding height lower than a protruding height of the protruding portions, the ridge extending along an outer circumference of the suction hole.

According to the present invention, the protruding height of the ridge is set to be lower than the protruding height of the protruding portions, and one of the two non-woven fabric sheets that contacts the anvil roll by being held by suction is inclined diagonally downward from the protruding portion toward the ridge. Therefore, during the ultrasonic welding process, there is formed a space between the protruding portion and the ridge, the space being surrounded by the inclined non-woven fabric sheet and the anvil roll.

Therefore, during the ultrasonic welding process, even if the granular particles remain on the non-woven fabric sheet in the vicinity of the protruding portions, the non-woven fabric sheet that contacts the anvil roll and the granular particles together with the non-woven fabric sheet can escape into the space between the protruding portion and the ridge, and the granular particles will be prevented from getting caught between the protruding portion of the anvil roll and the horn.

Absorbent articles, as used in the present invention, refer to feminine sanitary products and incontinence pads, as well as parts such as absorbent bodies and absorbent cores, which are intermediate products of disposable diapers and pants. The non-woven fabric sheet is liquid-permeable and air-permeable.

BRIEF DESCRIPTION OF DRAWINGS

FIG. 2 is an exploded perspective view showing an absorbent article.

FIG. 3A is a partial enlarged plan view showing the absorbent article, FIG. 3B is a cross-sectional view thereof, and FIG. 3C is a cross-sectional view thereof showing the absorbent article in which two non-woven fabric sheets are separated from each other at low-strength bonded portions.

FIG. 4 is a side view showing a device for manufacturing the absorbent article.

FIG. 6A is a development view showing a part of the outer circumferential surface of the anvil roll unfolded onto a plane, and FIG. 6B is a longitudinal cross-sectional view showing a ring forming the outer circumferential portion of the anvil roll.

Figure 1:
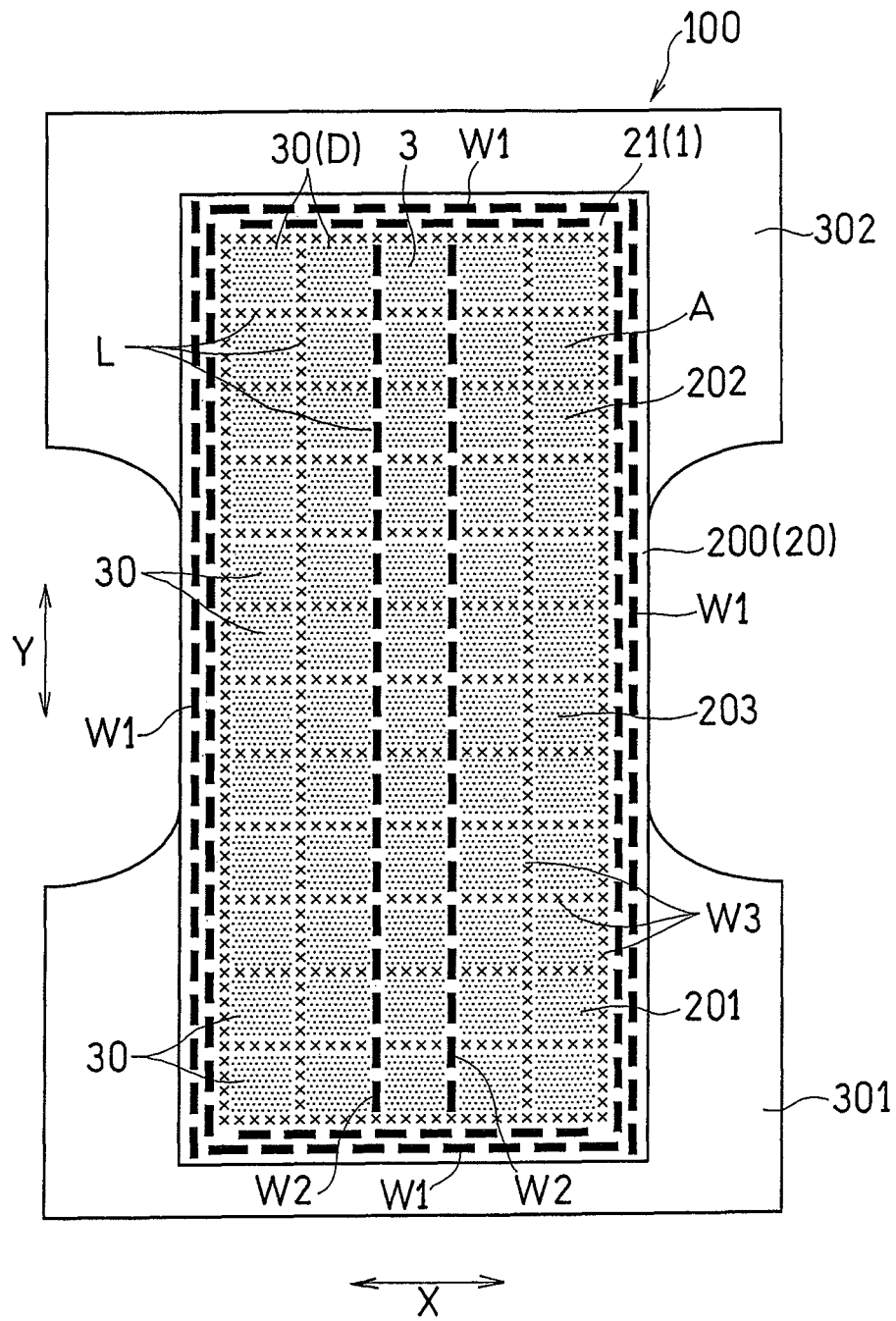
FIG. 1 is a plan view showing a worn article according to Embodiment 1 of the present invention.

Preferably, in the present invention, the anvil roll defines a groove extending along the ridge between the ridge and the plurality of protruding portions.

In this case, during the ultrasonic welding process, the granular particles and the non-woven fabric sheet that contacts the anvil roll can easily escape into the groove.

More preferably, the ridge is provided in a loop-shaped pattern so as to surround an entire circumference of the suction hole.

If the ridge is in a loop-shaped pattern, one of the two non-woven fabric sheets that contacts the anvil roll will likely be in contact with the ridge due to the suction force of the air drawn into the suction hole.

The "loop-shaped pattern" as used in the present invention is a concept including cases where the ridge is formed intermittently around the suction hole, as well as cases where the ridge is completely continuous.

Note that when the ridge is completely continuous, as compared with cases where it is intermittent, the suction force of the air will even less likely act upon the space between the protruding portion and the ridge. That is, if the ridge is formed intermittently, the suction force of the air will slightly act through between ridges.

More preferably, the ridge is formed so that when the first air is drawn from the suction hole, one of the two non-woven fabric sheets that contacts the anvil roll is in contact with the protruding portions and the ridge.

In this case, between the protruding portion and the ridge, the suction force of the air will less likely act upon the space formed between the non-woven fabric sheet and the anvil roll, and therefore the granular particles will less likely be drawn onto the non-woven fabric sheet around the protruding portion.

More preferably, the ridge is tapered so that a thickness of the ridge decreases as the ridge extends toward an outer end (tip) thereof in the radial direction.

The granular particles are likely to remain in the position of the ridge itself if the ridge has a large thickness, whereas if the ridge is tapered so that the outer end thereof is thin, the granular particles will unlikely remain on the ridge, and if the granular particles should remain, the granular particles sandwiched between the ridge and the horn will likely be crushed.

Moreover, as the ridge is tapered, it is possible to increase the cross-sectional area of the groove between the ridge and the protruding portion, which may make it easier for the granular particles to escape into the groove.

More preferably, the anvil roll defines discharge holes for discharging a second air to prevent the granular particles from being placed on portions of the non-woven fabric sheet corresponding to the plurality of protruding portions, each discharge hole being open on a surface of the protruding portion.

In this case, the discharge of the second air prevents the granular particles from remaining on the bonded portions, thereby making it likely that an intended bonded state or bonding strength will be obtained through the ultrasonic welding process.

More preferably, a plurality of suction holes are provided on the anvil roll and are placed in a predetermined pattern so as to define a plurality of placement areas in which aggregates of the granular particles are placed while being partitioned from one another.

In this case, the granular particles placed in the predetermined pattern will less likely be placed outside the placement areas. This will further reduce the possibility that the granular particles are sandwiched between the two non-woven fabric sheets outside the placement areas.

DESCRIPTION OF EMBODIMENTS

The present invention will be understood more clearly from the description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiment 1

Embodiment 1 of the present invention will now be described with reference to the drawings.

FIGS. 1 to 9 show Embodiment 1.

Worn article 100:

As shown in FIG. 1, the worn article 100 of the present embodiment includes an absorbent body (an example of the absorbent article) 200, a front around-torso member 301, and a back around-torso member 302. The absorbent body 200 includes a front portion 201 covering the front torso of the wearer, a back portion 202 covering the back torso of the wearer, and a crotch portion 203 covering the crotch between the front portion 201 and the back portion 202.

The crotch portion 203 is continuous with the front portion 201 and the back portion 202, and extends in the longitudinal direction Y perpendicular to the girth direction X. The front around-torso member 301 and the back around-torso member 302 may be bonded together when worn, or may be pre-bonded before being worn.

The absorbent body 200 may be provided with three-dimensional gathers (not shown).

The absorbent body 200 may include around-leg portions narrowed in conformity with the legs of the wearer.

Moreover, portions of the absorbent body 200 to be the around-leg portions may be provided with elastic members for fitting the worn article 100 to the wearer. The elastic members may be, for example, a plurality of rubber threads, rubber tapes, a film, a material including a thermoplastic resin, or the like. These materials may be provided in the front portion 201 and the back portion 202 as elastic members for fitting the worn article 100 to the wearer.

As shown in FIG. 2, the absorbent body 200 includes a top sheet 21 to be in contact with the skin surface of the wearer, and a cover sheet 22 and an absorbent core 23 to be not in contact with the skin surface. The top sheet 21 and the cover sheet 22 of FIG. 3B (welded portion) are welded together along lattice-shaped welded lines L, L extending in the length and width directions as shown in FIG. 3A, thereby forming a sandwich structure in which the core 23 is sandwiched between adjacent welded lines L, L.

That is, as shown in FIG. 3A, the core 23 is surrounded by the top sheet 21 and the cover sheet 22 welded together along the welded lines L, L.

Note that welded positions are denoted by 'xx' or small black rectangles in different figures.

The top sheet 21 and the cover sheet 22 of FIG. 3B are formed by a non-woven fabric sheet that is liquid-permeable and air-permeable. A non-liquid-permeable back sheet 24 is attached to the back surface of the cover sheet 22, and the absorbent body 200 is covered by the back sheet 24.

The core 23 includes a large number of absorbent granular particles 3. The granular particles 3 are made of a well-known absorbent high-molecular polymer whose average granular diameter is typically about 10 μm to about 1,000 μm before absorbing moisture and which swell after absorbing moisture to a volume several times to several hundreds of times larger.

Note that the granular particles 3 are denoted by a large number of minute dots in FIGS. 1 to 4.

The core 23 includes aggregate groups 30 placed in a large number of placement areas D, the aggregate groups 30 each having an aggregate of a large number of granular particles 3. The aggregate groups 30, 30 are separately arranged in the placement areas D, D partitioned by lattice-shaped welded lines L, L extending in the length and width directions. That is, the placement areas D, D, in which the aggregate groups 30, 30 are placed, are partitioned from one another by the welded lines L, L.

In other words, each aggregate group 30 is composed of an aggregate of a large number of granular particles 3, and the aggregate groups 30 are arranged in the length and width directions with welded lines L, L therebetween, as shown in FIG. 3A. As shown in FIG. 3A, a larger number (three or more) of aggregate groups are arranged in the length and width directions.

A welded line L does not need to be completely continuous, and may be an intermittent array of welded positions such that the granular particles 3 in one aggregate group 30 cannot easily move into other aggregate groups 30.

That is, the welded lines L, L may be formed in such a manner that it is possible to suppress the movement of granular particles 3 from one of the aggregate groups 30, arranged in a predetermined pattern, into another.

The arrangement of the aggregate groups 30 may be any predetermined pattern, and does not need to be a regular array extending in the length and width directions. The number (volume) of granular particles 3 contained in each aggregate group 30 does not need to be generally equal to that in other groups, and the number (volume) of granular particles 3 may be determined based on the amount of body fluid to be discharged in each aggregate group 30.

As shown in the enlarged view of FIG. 3A, the aggregate groups 30 may be rectangular or circular, and the length of each side or the diameter thereof may be some millimeters to some tens of millimeters. The pitch at which the aggregate groups 30, 30 are placed may be about 10 mm to about ten-odd mm.

In the present embodiment, the welded lines L include first high-strength bonded portions W1, second high-strength bonded portions W2, and low-strength bonded portions W3, as shown in FIG. 3A.

As shown in FIG. 1, the first high-strength bonded portions W1 are formed in a loop-shaped pattern along the periphery of the absorbent article 200, and the first high-strength bonded portions W1 are welded positions (solid black small rectangles) provided in a multi-line staggered array in which they are intermittently formed close to one another, for example. The first high-strength bonded portions W1 prevent the granular particles 3, a body fluid, or the granular particles 3 having absorbed a body fluid, from leaking out through between the top sheet 21 and the cover sheet 22.

As shown in FIG. 3A, the low-strength bonded portions W3 are placed in a lattice-shaped pattern, for example, in an inner area A surrounded by the first high-strength bonded portions. W1 in a loop-shaped pattern, thereby partitioning the inner area A into a plurality of placement areas D as described above. The low-strength bonded portions W3 are denoted by 'xx' in the figures.

The second high-strength bonded portions W2 are formed in a linear pattern, for example, in the inner area A, and may be placed between low-strength bonded portions W3.

The second high-strength bonded portions W2 are denoted as solid black rectangles in the figures.

At the first high-strength bonded portions W1 and the second high-strength bonded portions W2, the top sheet 21 and the cover sheet 22, which are the two non-woven fabric sheets, are welded together with a large welding force such that they will not be separated from each other even when the granular particles 3 swell to apply a separating force to the bonded positions between the sheets 21 and 22.

At the low-strength bonded portions W3, the two sheets of the top sheet 21 and the cover sheet 22 are welded together with such a small welding force that when the granular particles 3 swell to apply a separating force to bonded positions between the top sheet 21 and the cover sheet 22, the sheets 21 and 22 will be separated from each other at the bonded positions.

That is, the welding force between the non-woven fabric sheets 21 and 22 at the low-strength bonded portions W3 is smaller than the welding force at the first and second high-strength bonded portions W1 and W2.

Therefore, when a body fluid from the wearer is absorbed by the granular particles 3 through the top sheet 21 of FIG. 3B, the granular particles 3 swell substantially so that a pressure (separating force) acts upon the space between the top sheet 21 and the cover sheet 22 as shown in FIG. 3B, thereby separating the top sheet 21 and the cover sheet 22 from each other at the low-strength bonded portions W3 as shown in FIG. 3C, thus enabling further liquid absorption by the granular particles 3.

Thus, even where the absorbent body 200 has a small thickness before being used, it is possible to absorb a large amount of body fluid.

On the other hand, the second high-strength bonded portions W2 remain bonded even after the granular particles 3 swell to apply the separating force. This restricts the granular particles 3, having swollen and become heavier, from moving freely in the inner area A.

Note that the non-woven fabric sheet may be a thermoplastic resin non-woven fabric sheet such as polypropylene, polyethylene, polyester, or the like, and it may also be a non-woven fabric sheet obtained by blending together non-thermoplastic fibers such as cotton or rayon with thermoplastic resin fibers.

Next, a device for manufacturing the absorbent body 200 will be illustrated.

As shown in FIG. 4, the present device includes a dispenser device 5, first and second introduction rolls 71 and 72, and an ultrasonic horn 81, arranged around an anvil roll 4.

The first and second introduction rolls 71 and 72 are rolls for introducing a carrier web 1 and a cover web 2, respectively, onto the outer circumference of the anvil roll 4.

The top sheet 21 and the cover sheet 22 of the absorbent body 200 (FIG. 2) are produced from the carrier web 1 and the cover web 2, respectively.

The anvil roll 4 carries the carrier web 1 along a predetermined carrying path while holding by suction a first surface 11 of the air-permeable carrier web 1 on a carrying surface 41. The first surface 11 forms the skin surface to be in contact with the skin of the wearer.

The dispenser device 5 dispenses myriads of granular particles 3 onto a second surface 12 opposite to the first surface 11 of the carrier web 1 being carried, downstream of the first introduction roll 71.

The myriads of granular particles 3 are dispensed intermittently or continuously so that a predetermined amount is dispensed per unit area of the carrier web 1.

Figure 5:
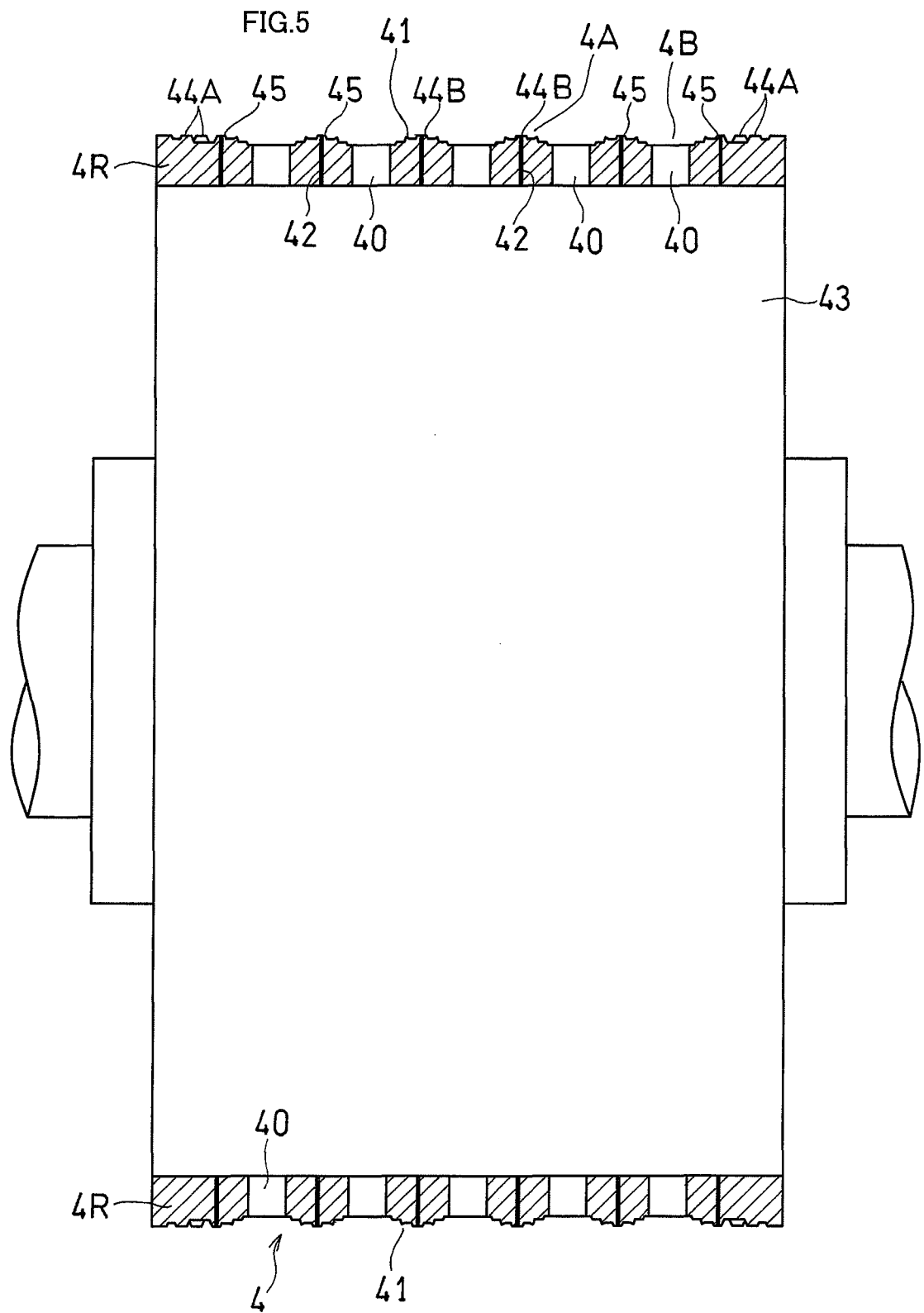
FIG. 5 is a longitudinal cross-sectional view, which is partially a cross-sectional view, showing an example of an anvil roll.

As shown in FIGS. 5 to 7, a large number of suction holes 40 (an example of the placement device) are provided (open) in suction areas 4B of the carrying surface 41. Each suction hole 40 communicates with a suction source (negative pressure source) (not shown), and draws a first air a1 into the suction hole 40 through the carrier web 1 of FIG. 8, thereby holding by suction the granular particles 3 on the second surface 12 of the carrier web 1.

As shown in FIGS. 6A and 6B, there are a plurality of suction holes 40, and the suction holes 40 are provided so as to define a plurality of placement areas D of FIG. 1, which are placed in a predetermined pattern. The plurality of placement areas D are areas in which aggregates of granular particles are placed while being partitioned from one another.

As shown in FIGS. 6A and 6B, discharge holes 42 (an example of the placement device) are provided (open) in non-suction areas 4A, where the suction is absent, including first and second protruding portions 44B and 45 between the suction holes 40 and the suction holes 40, on the anvil roll 4. Each discharge hole 42 is open in the first and second protruding portions 44B and 45 of the carrying surface 41 for discharging a second air α2.

On the other hand, the first protruding portions 44A are provided on the anvil roll 4 at positions corresponding to the first high-strength bonded portions W1 (FIG. 1) along the periphery of the absorbent body 200. The discharge holes 42 may be absent in first protruding portions 44A.

The provision of the discharge holes 42 may not be necessary in the first protruding portions 44A because substantially no granular particles 3 are dispensed along the periphery of the carrier web 1 if the width over which the granular particles 3 are dispensed from the dispenser device 5 is substantially the same as the width over which the granular particles 3 are placed in the absorbent body 200.

Note that the first protruding portions 44A may be provided with the discharge holes 42, similar to the first protruding portion 44B and the second protruding portion 45.

Each discharge hole 42 communicates with a positive pressure source (not shown) of the air, and discharges the second air α2 from the discharge hole 42 toward the second surface 12 of the carrier web 1. Thus, the granular particles 3 are blown away off the non-suction area 1A on the carrier web 1 of FIG. 8 by the second air α2 having passed through the carrier web 1 via the second surface 12.

The suction holes 40 and the discharge holes 42 prevent the granular particles 3 from being placed on the carrier web 1 over the protruding portions 44A (FIG. 6B), 44B and 45.

Figure 8:
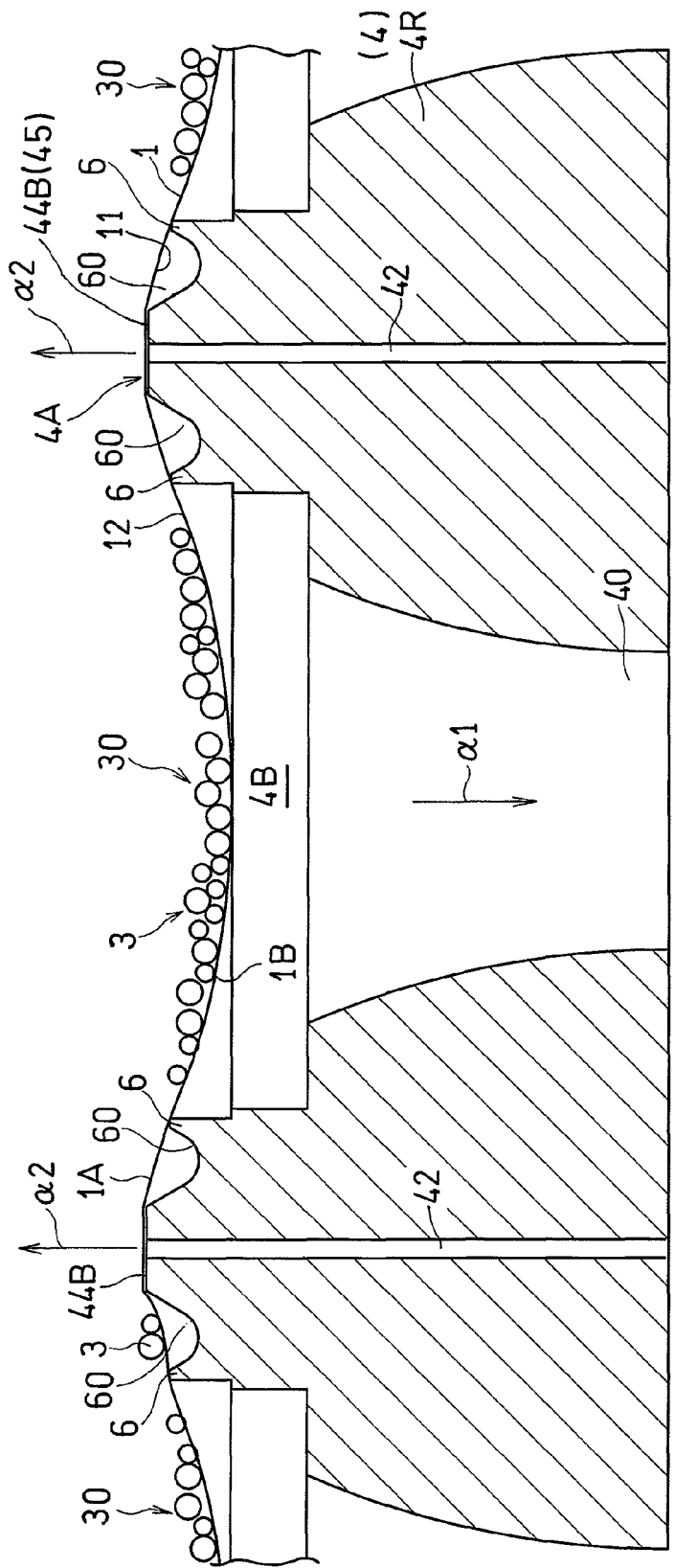
FIG. 8 is a cross-sectional view showing an anvil on an enlarged scale.

As shown in FIGS. 4 and 8, the granular particles 3 dispensed from the dispenser device 5 onto the carrier web 1 are partitioned into the aggregate groups 30 by the placement device (the suction holes 40 and the discharge holes 42) as the carrier web 1 is carried downstream. That is, the suction holes 40 sucks the granular particles 3, together with the non-woven fabric sheet 1, in order to carry the non-woven fabric sheet 1 and to prevent the granular particles 3 from being placed on the non-woven fabric sheet 1 over the protruding portions 44A, 44B and 45.

After the granular particles 3 are placed on the carrier web 1, the second introduction roll 72 of FIG. 4 introduces the cover web 2 onto the carrying path at a position of the carrier web 1 downstream in the carrying path in order to produce a sandwich structure 20 (FIG. 7B) in which the second surface 12 of the carrier web 1 and the granular particles 3 are covered by the cover web 2.

The anvil roll 4 carries the sandwich structure 20 as described above.

That is, as shown in FIG. 4, the cover web 2 is introduced after the granular particles 3 are partitioned into the aggregate groups 30 on the carrier web 1. The cover web 2 covers portions of the second surface 12 of the carrier web 1 where the granular particles 3 are absent, and the granular particles 3 placed on the carrier web 1. Thus, the sandwich structure 20 is produced.

Note that due to the first air α1 drawn into the suction holes 40 of the anvil roll 4 of FIG. 6B, the cover web 2 introduced over the second surface 12 and the granular particles 3 are bowed into the anvil roll 4.

The anvil roll 4 may include a roll body 43 and a ring-shaped anvil 4R removably attached over the outer circumference of the roll body 43, as shown in FIG. 5. Then, it is possible to easily change the placement pattern, or the like.

As shown in FIGS. 6A to 7B, a large number of first protruding portions 44A and 44B and second protruding portions 45 are provided around the suction holes 40 of the anvil 4R. These protruding portions 44A, 44B and 45 are protruding outward in the radial direction of the anvil roll 4, and are facing the ultrasonic horn 81 (FIG. 4) with the sandwich structure 20 therebetween as the anvil roll 4 rotates.

The first protruding portions 44B (or the first protruding portions 44A) of FIG. 6B are protruding outward in the radial direction toward the horn 81 (FIG. 4) slightly more than the second protruding portion 45. This is so that the first protruding portions 44A and 44B form the high-strength bonded portions W1 and W2, and the second protruding portions 45 form the low-strength bonded portions W3.

As is partially shown in FIG. 6A, the first protruding portions 44A are placed on the anvil roll 4 so that the first high-strength bonded portions W1 (FIG. 1) are formed in a loop-shaped pattern along the periphery of the absorbent body 200.

On the other hand, the first protruding portions 44B of FIG. 6A are placed on the anvil roll 4 so as to form the second high-strength bonded portions W2 in the inner area A of FIG. 1.

The second protruding portions 45 of FIG. 6A are placed on the anvil roll 4 so that the low-strength bonded portions W3 are formed in the inner area A surrounded by the first high-strength bonded portions W1.

That is, the first high-strength bonded portions W1, the second high-strength bonded portions W2 and the low-strength bonded portions W3 are formed along positions where the first protruding portions 44A, the first protruding portions 44B and the second protruding portions 45 are placed, respectively.

As shown in FIG. 4, the ultrasonic horn 81 gives the vibration energy to the webs (non-woven fabric sheets) 1 and 2 in cooperation with the ring-shaped anvil 4R (FIG. 5), which forms the carrying surface 41 of the anvil roll 4, downstream of the second introduction roll 72 in the carrying path of the carrier web 1. Thus, the carrier web 1 and the cover web 2 are welded together at the first protruding portions 44B (44A) and the second protruding portions 45 of FIG. 7B.

With welding (sealing) using ultrasonic vibrations, mechanical vibrations are ultrasonically transmitted to the horn 81 of FIG. 4, so that thermoplastic non-woven fabric sheets pass through between the horn 81 and the anvil 4R while being pressurized, thereby welding the non-woven fabric sheets (the carrier web 1 and the cover web 2) with each other by frictional heat. Therefore, a seal failure is likely to occur if granular particles 3, which are foreign matters, remain between the webs 1 and 2 in the non-suction areas 4A of FIG. 6A.

Next, an important part of the present invention will be described.

Figure 7A:
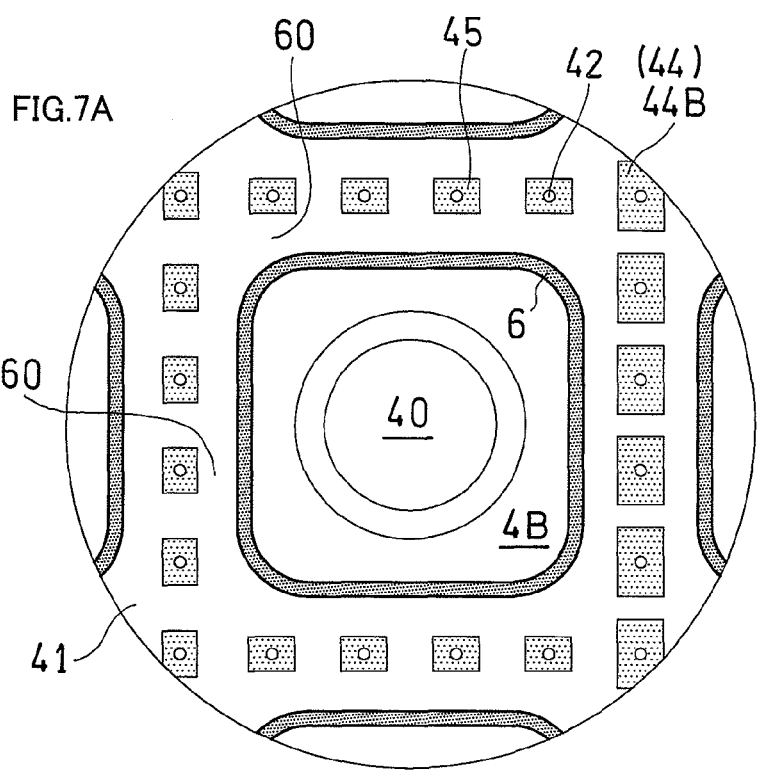
FIGS. 7A and 7B are development views each showing, on an enlarged scale, a part of the anvil roll.

As shown in FIGS. 8 and 7A (indicated by dense dotting), a ridge 6 is provided along the periphery of a suction hole 40 so as to extend all around the circumference of the suction holes 40, for example.

The ridge 6 is formed so that when the first air a1 is drawn from the suction hole 40, the non-woven fabric sheet 1 (of the two non-woven fabric sheets 1 and 2), which contacts the anvil roll 4, is in contact with the protruding portions 44B and 45 and the ridge 6, as shown in FIG. 8.

That is, the ridge 6 is provided between the plurality of protruding portions 44B and 45 and the suction hole 40 as shown in FIG. 7A, and the ridge 6 protrudes outward in the radial direction of the anvil roll 4 of FIG. 8 and extends along the outer circumference of the suction hole 40 with its protruding height lower than a protruding height of the protruding portions 44B and 45.

Figure 7B:
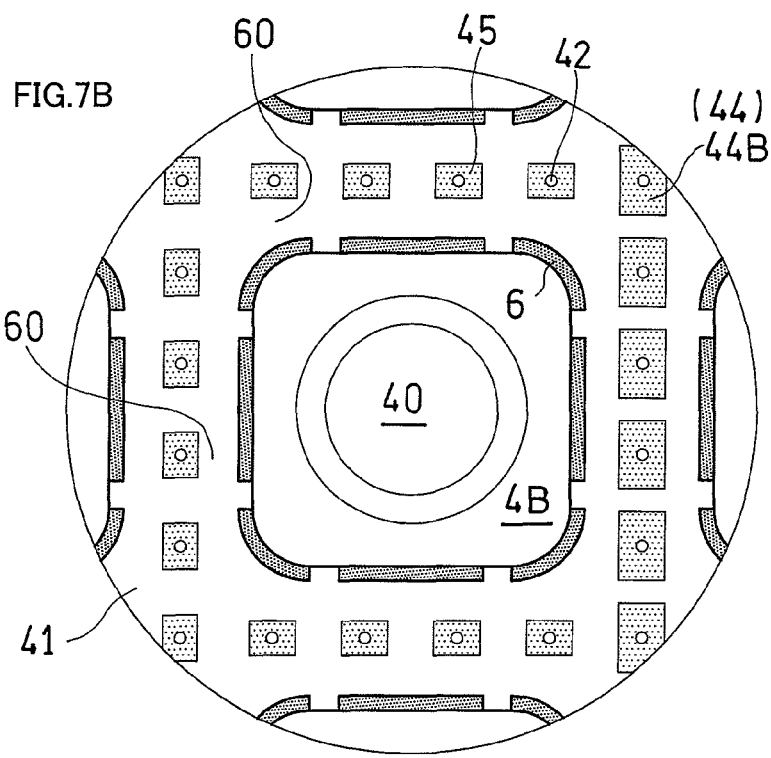
Figure 9A:
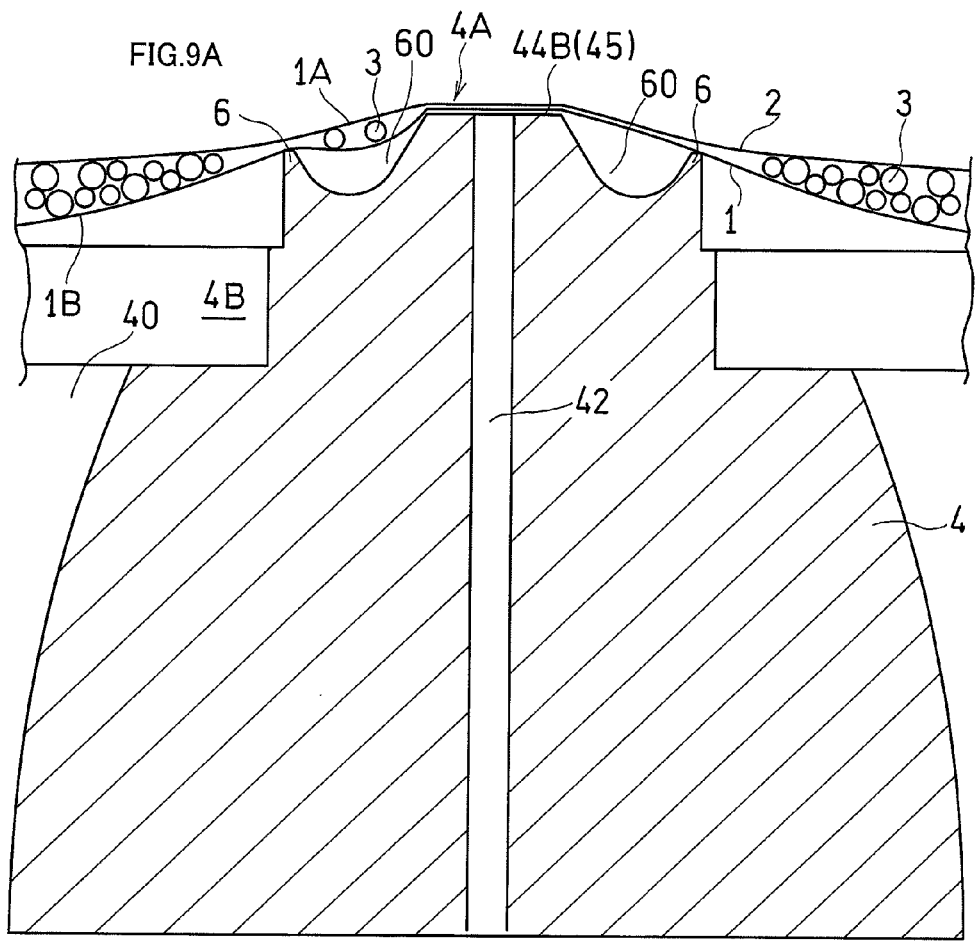
FIG. 9A is a cross-sectional view showing one protruding portion of the anvil on a more enlarged scale.

In FIGS. 7A and 7B, a groove 60 is provided in the anvil roll 4 extending along the ridge 6 between the ridge 6 and the plurality of protruding portions 44B and 45. As shown in FIG. 9A, the ridge 6 may be tapered so that the thickness of the ridge 6 decreases toward the outer end (tip) thereof in the radial direction.

As shown in FIG. 8, the first surface 11 of the carrier web 1 held by suction on the anvil roll 4 (4R) is in contact with the ridge 6 and the protruding portion 44B (45). Between the carrier web 1 and the anvil roll 4 in contact with each other, a portion corresponding to the groove 60 remains as a space.

While the ridge 6 of FIG. 7A is provided continuously so as to surround the entire circumference of the suction hole 40 in the present embodiment, it may be provided intermittently in a loop-shaped pattern as shown in FIG. 7B.

Next, an outline of a method for manufacturing the sandwich structure 20 will be described.

As shown in FIG. 4, the carrier web 1 is introduced onto the anvil roll 4 by the first introduction roll 71, and the carrier web 1 is carried along a predetermined carrying path, i.e., the carrying surface 41 of the carrying drum 4, while the first surface 11 of the carrier web 1 is held by suction on the carrying surface 41 of the anvil roll 4.

Between the first introduction roll 71 and the second introduction roll 72, a large number of granular particles 3 are dispensed from the dispenser device 5 onto the second surface 12, opposite to the first surface 11, of the carrier web 1 which is being carried. The dispensed granular particles 3 form a layer on the second surface 12.

As the first air α1 is drawn toward the suction holes 40 formed in the anvil 4R shown in FIG. 8, the dispensed granular particles 3 are held by suction on the carrier web 1.

Note that an airflow deflector may be provided opposing the second surface 12 of the carrier web 1, the airflow deflector giving at least a part of the first air α1 a flow component flowing in a direction along the second surface 12 of the carrier web 1. (PCT/JP2012/52371)

The layer of granular particles 3 of FIG. 4 may be dispensed intermittently for each absorbent body 200 (FIG. 1).

The layer of granular particles 3 may have a greater thickness in the central part of the layer than in opposite end portions of the layer in the axial direction of the anvil roll 4. Alternatively, the layer of granular particles 3 may have a smaller thickness along the periphery of one absorbent body 200 (FIG. 1) and have a greater thickness in the center or the vicinity thereof.

In FIG. 8, the first air α1 is drawn through the carrier web 1 by a plurality of suction holes 40 formed in the carrying surface 41, as described above, thereby holding by suction some of the granular particles 3 on the second surface 12 of the carrier web 1.

On the other hand, while the first air α1 is drawn, the second air α2 is discharged toward the second surface 12 of the carrier web 1 from the discharge holes 42 open in the non-suction areas 4A including the protruding portions 44B and 45 of the carrying surface 41.

By simultaneously drawing the first air α1 and discharging the second air α2, the granular particles 3 on the non-suction areas 1A are blown away by the second air α2 having passed through the carrier web 1 via the second surface 12, and the blown granular particles 3 are drawn by the first air α1 toward the suction areas 1B over the suction holes 40.

As shown in FIG. 8, the granular particles 3 in the non-suction areas 1A on the carrier web 1 move into the suction areas 1B so that the granular particles 3 are placed in a predetermined pattern on the carrier web 1.

That is, some granular particles 3 in the non-suction areas 1A move toward other granular particles 3 being sucked and held in the suction areas 1B. As a result, as shown in FIG. 1, the aggregate groups 30, each including a plurality of granular particles 3, are placed on the carrier web 1 separately in the placement areas D partitioned in a predetermined pattern.

As shown in FIG. 4, after the granular particles 3 dispensed from the dispenser device 5 are placed in a predetermined pattern (separately in the placement areas D) on the carrier web 1, the second surface 12 of the carrier web 1 where the granular particles 3 are absent, and the granular particles 3 placed on the carrier web 1 are covered by the cover web 2 introduced by the second introduction roll 72, thereby producing the sandwich structure 20.

Then, as the sandwich structure 20 continues to be rotated by the carrying surface 41 to reach the ultrasonic horn 81 of FIG. 4, the carrier web 1 and the cover web 2 are ultrasonically welded together at positions corresponding to the non-suction areas 1A of FIG. 2.

Thus, the predetermined pattern of the granular particles 3 is maintained. After welding together the webs 1 and 2, the suction of the suction holes 40 and the discharge from the discharge holes 42 of FIG. 6B may be stopped. During the welding process, the back sheet 24 of FIG. 3B is also welded onto the cover web 2, but the back sheet 24 may be bonded with an adhesive onto the cover web 2 after the carrier web 1 and the cover web 2 are welded together.

Then, the sandwich structure 20 is cut into individual worn articles, i.e., into individual absorbent bodies 200 of FIG. 1.

Next, advantages of the provision of the ridge 6 of the present invention will be described.

As described above, the granular particles 3 of FIG. 8 will be gathered in the suction area 1B on the carrier web 1, and will less likely remain in the non-suction area 1A outside the suction area 1B. However, since the granular particles 3 have a small mass, it is difficult to control the placement of the granular particles 3, and the granular particles 3 may in some cases remain in the vicinity of the protruding portion 44B in a left part of FIG. 8 or the protruding portion 44B (45) of FIG. 9A.

Moreover, due to minute surface irregularities (concave and convex), or the like, of the non-woven fabric sheets, the granular particles 3 may get caught on the non-woven fabric sheet as they travel from the non-suction area 1A toward the suction area 1B, thus remaining in the vicinity of the protruding portion 44B (45).

In such a case, since the ridge 6 is surrounding the protruding portion 44B (45) in the vicinity thereof as shown in FIG. 8, a portion corresponding to the groove 60 remains as a space between the carrier web 1 and the anvil roll 4, between the ridge 6 and the protruding portion 44B (45). Thus, as shown in FIG. 9A, between the ridge 6 and the protruding portion 44B, 45, the granular particles 3 on the carrier web 1 can escape into the gap therebetween, i.e., escape downward into the groove 60 together with the carrier web 1, during the ultrasonic welding process. Therefore, the granular particles 3 will unlikely be caught between the horn 81 and protruding portions.

For example, even if the horn 81 (FIG. 4) ultrasonically vibrates, with the horn 81 facing the protruding portion 44B, 45 and with the granular particles 3 remaining on a portion of the carrier web 1 corresponding to the groove 60, the granular particles 3 on the carrier web 1 can escape into (move toward) the groove 60. Therefore, the granular particles 3 will not be sandwiched between the anvil roll 4 and the horn 81 (FIG. 4) in the vicinity of the protruding portion 44B (45), and therefore will not get caught therebetween.

In the present embodiment, the cross-sectional shape of the groove 60 flares outwardly in the radial direction of the anvil roll 4, and the granular particles 3 on the carrier web 1 at a position corresponding to the groove 60 will therefore easily escape into a deep portion of the groove 60 (in the direction toward the center of the anvil roll).

Moreover, the air suction force will unlikely act upon the groove 60 (inside the space) covered by the carrier web 1 between the protruding portion 44B (45) and the ridge 6. Therefore, the granular particles 3 will unlikely be drawn onto the carrier web 1 around the protruding portion 44B (45), making it unlikely that the movement of the granular particles 3 toward the suction area 1B is inhibited.

Figure 9B:
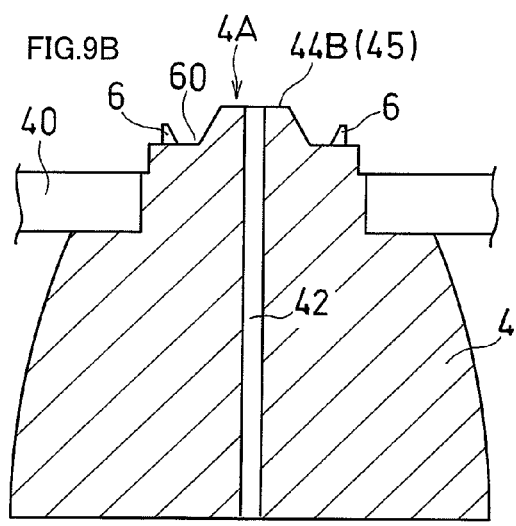
FIG. 9B is an enlarged cross-sectional view showing another example of a ridge.

Note that the ridge 6 does not need to be provided along the outer circumference of the suction hole 40, but may be provided at a position slightly separated from the suction hole 40 as shown in FIG. 9B.

While preferred embodiments have been described above with reference to the drawings, obvious variations and modifications will readily occur to those skilled in the art upon reading the present specification.

Regarding the bonded portions, for example, only one of the low-strength bonded portions and the high-strength bonded portions may be provided. The discharge holes may be absent.

As used in the present invention, "a plurality of granular particles" is a concept including cases where a powdery material is mixed with a plurality of granular particles, as well as cases where they are made only of an aggregate or aggregates of a granular material.

Thus, such changes and modifications are deemed to fall within the scope of the present invention, which is defined by the appended claims.

INDUSTRIAL APPLICABILITY

The present invention is applicable to disposable worn articles, such as feminine sanitary products and incontinence pads, as well as disposable diapers and disposable pants.

REFERENCE SIGNS LIST

1: Carrier web, 1A: Non-suction area, 1B: Suction area, 11: First surface, 12: Second surface
2: Cover web, 20: Sandwich structure, 21: Top sheet (non-woven fabric sheet), 22: Cover sheet (non-woven fabric sheet), 23: Core, 24: Back sheet
3: Granular particles, 30: Aggregate group, D: Placement area
4: Anvil roll, 4A: Non-suction area, 4B: Suction area, 40: Suction hole, 41: Carrying surface, 42: Discharge holes (an example of the placement device), 4R: Anvil, 43: Roll body, 44A, 44B: First protruding portion, 45: Second protruding portion
5: Dispenser device
6: Ridge, 60: Groove
71: First introduction roll, 72: Second introduction roll
81: Ultrasonic horn
100: Worn article, 200: Absorbent body (absorbent article), 201: Front portion, 202: Back portion, 203: Crotch portion, 301: Front around-torso member, 302: Back around-torso member
A: Inner area
$\alpha 1$: First air, $\alpha 2$: Second air
X: Girth direction, Y: Longitudinal direction
W1: First high-strength bonded portion, W2: Second high-strength bonded portion, W3: Low-strength bonded portion

The invention claimed is:

1. A device for manufacturing an absorbent article having a plurality of granular particles capable of absorbing a body fluid between two liquid-permeable non-woven fabric sheets facing each other, the manufacturing device comprising:
   an anvil roll for carrying the two non-woven fabric sheets while the two non-woven fabric sheets are laid on each other;
   a plurality of protruding portions formed on the anvil roll so as to protrude outward in a radial direction of the anvil roll; and
   a horn for ultrasonically vibrating so that the two non-woven fabric sheets are bonded together between the horn and the plurality of protruding portions, thereby forming bonded portions,
   wherein the anvil roll defines:
   at least one suction hole for drawing a first air, through the non-woven fabric sheets, together with the granular particles and the non-woven fabric sheets, so as to carry the non-woven fabric sheets and to prevent the granular particles from being placed on the non-woven fabric sheets over the protruding portions; and
   a ridge provided between the plurality of protruding portions and the suction hole, the ridge protruding outward in the radial direction of the anvil roll with a protruding height lower than a protruding height of the protruding portions, the ridge extending along an outer circumference of the suction hole.

2. The manufacturing device according to claim 1, wherein the anvil roll defines a groove extending along the ridge between the ridge and the plurality of protruding portions.

3. The manufacturing device according to claim 2, wherein the ridge is provided in a loop-shaped pattern so as to surround an entire circumference of the suction hole.

4. The manufacturing device according to claim 3, wherein the ridge is formed so that when the first air is drawn from the suction hole, one of the two non-woven fabric sheets that contacts the anvil roll is in contact with the protruding portions and the ridge.

5. The manufacturing device according to claim 4, wherein the ridge is tapered so that a thickness of the ridge decreases as the ridge extends toward an outer end thereof in the radial direction.

6. The manufacturing device according to claim 5, wherein the anvil roll defines discharge holes for discharging a second air to prevent the granular particles from being placed on portions of the non-woven fabric sheets corresponding to the plurality of protruding portions, each of the discharge holes being open on a surface of the protruding portions.

7. The manufacturing device according to claim 6, wherein a plurality of the suction holes are provided on the anvil roll and are placed in a predetermined pattern so as to define a plurality of placement areas in which aggregates of the granular particles are placed while being partitioned from one another.

* * * * *